US009782327B2

(12) United States Patent
Miceli et al.

(10) Patent No.: US 9,782,327 B2
(45) Date of Patent: Oct. 10, 2017

(54) COMPLIANCE PILL TRAY SYSTEM

(71) Applicant: Tri State Distribution, Inc., Sparta, TN (US)

(72) Inventors: David A. Miceli, Reno, NV (US); Joseph A. Miceli, Spencer, TN (US)

(73) Assignee: Tri State Distribution, Inc., Sparta, TN (US)

( * ) Notice: Subject to any disclaimer, the term of this patent is extended or adjusted under 35 U.S.C. 154(b) by 0 days.

(21) Appl. No.: 15/221,783

(22) Filed: Jul. 28, 2016

(65) Prior Publication Data

US 2016/0331642 A1 Nov. 17, 2016

Related U.S. Application Data

(63) Continuation-in-part of application No. 14/323,253, filed on Jul. 3, 2014, now Pat. No. 9,427,377.

(60) Provisional application No. 62/328,883, filed on Apr. 28, 2016.

(51) Int. Cl.
| | | |
|---|---|---|
| *A61J 7/04* | (2006.01) | |
| *A61J 1/03* | (2006.01) | |
| *A61J 7/00* | (2006.01) | |
| *G06F 19/00* | (2011.01) | |

(52) U.S. Cl.
CPC .................. *A61J 7/04* (2013.01); *A61J 1/03* (2013.01); *A61J 7/0069* (2013.01); *A61J 7/0084* (2013.01); *G06F 19/3462* (2013.01); *A61J 2205/30* (2013.01)

(58) Field of Classification Search
CPC .......... A61J 7/04; A61J 7/0418–7/0481; A61J 7/0069; A61J 7/0084; A61J 1/03; A61J 2205/30; G06F 19/3456–19/3475; G08B 21/24
See application file for complete search history.

(56) References Cited

U.S. PATENT DOCUMENTS

| | | | |
|---|---|---|---|
| 4,473,156 A | 9/1984 | Martin | |
| 4,749,085 A | 6/1988 | Denney | |
| 5,014,798 A * | 5/1991 | Glynn | G01G 11/006 177/132 |
| 5,159,581 A * | 10/1992 | Agans | G04G 15/006 206/538 |
| 5,408,443 A * | 4/1995 | Weinberger | G06F 19/3462 221/3 |
| 5,431,450 A | 7/1995 | Coleman | |
| 5,826,217 A * | 10/1998 | Lerner | A61J 7/0481 221/15 |
| 6,294,999 B1 * | 9/2001 | Yarin | A61J 7/0481 340/573.1 |
| 6,375,956 B1 * | 4/2002 | Hermelin | A61J 7/04 206/528 |
| 6,380,858 B1 * | 4/2002 | Yarin | A61J 7/0481 128/903 |
| 6,464,506 B1 | 10/2002 | Welles | |

(Continued)

*Primary Examiner* — Hai Phan
*Assistant Examiner* — Orlando Bousono
(74) *Attorney, Agent, or Firm* — Luedeka Neely Group, PC

(57) ABSTRACT

A prescription compliance system including a pill tray having a plurality of sequence compartments within a frequency section and dosage tables on prescription container systems that provide graphical dosage instruction information for the patient in dosing each of the sequence compartments of the pill tray with a plurality of prescribed medications.

21 Claims, 14 Drawing Sheets

(56) References Cited

U.S. PATENT DOCUMENTS

| | | |
|---|---|---|
| 6,550,618 B2 | 4/2003 | Peterson |
| 7,926,850 B1 | 4/2011 | Muncy et al. |
| 8,174,370 B1 | 5/2012 | Fulmer-Mason |
| 8,193,918 B1* | 6/2012 | Shavelsky .................. A61J 7/04 340/309.16 |
| 8,336,917 B2 | 12/2012 | Doiron |
| 8,799,016 B1* | 8/2014 | Cohan ................. G06F 19/3456 705/2 |
| 2002/0027507 A1* | 3/2002 | Yarin .................... A61J 7/0481 340/573.1 |
| 2002/0067270 A1* | 6/2002 | Yarin .................... A61J 7/0481 340/573.1 |
| 2002/0118604 A1* | 8/2002 | Sharma ..................... G04F 3/02 368/10 |
| 2004/0133305 A1* | 7/2004 | Jean-Pierre ......... G06F 19/3462 700/231 |
| 2004/0188998 A1 | 9/2004 | Henthorn |
| 2004/0243445 A1* | 12/2004 | Keene ................. G06F 19/3456 705/2 |
| 2005/0109658 A1 | 5/2005 | Bindford |
| 2005/0139506 A1* | 6/2005 | Lorenzato ................. A61J 7/04 206/534 |
| 2005/0150806 A1* | 7/2005 | Lorenzato ................. A61J 7/04 206/534 |
| 2005/0183982 A1 | 8/2005 | Giewercer |
| 2005/0267356 A1* | 12/2005 | Ramasubramanian ........................... G06F 19/3462 600/411 |
| 2005/0280257 A1* | 12/2005 | Nijjer ....................... B42D 5/04 283/2 |
| 2007/0023318 A1 | 2/2007 | Mauk |
| 2008/0027291 A1* | 1/2008 | Williams-Hartman ............................. A61J 7/0481 600/300 |
| 2008/0054007 A1* | 3/2008 | Mador .................. A61J 7/0481 221/1 |
| 2008/0077439 A1 | 3/2008 | Guion |
| 2008/0162188 A1 | 7/2008 | Kripalani et al. |
| 2008/0312965 A1* | 12/2008 | Meshginpoosh ..... G06F 19/322 705/3 |
| 2008/0312966 A1* | 12/2008 | Meshginpoosh ...... G06Q 50/22 705/3 |
| 2009/0039640 A1* | 2/2009 | Nijjer ....................... B42D 5/04 283/2 |
| 2009/0052283 A1* | 2/2009 | Puzia .................... A61J 7/0472 368/10 |
| 2009/0299522 A1* | 12/2009 | Savir ..................... A61J 7/0084 700/240 |
| 2010/0206765 A1 | 8/2010 | Fonte |
| 2012/0029693 A1* | 2/2012 | Bear ...................... A61J 7/0481 700/244 |
| 2013/0002795 A1* | 1/2013 | Shavelsky ................. A61J 7/04 348/14.01 |
| 2013/0018503 A1* | 1/2013 | Carson .................... B65B 57/16 700/216 |
| 2013/0030566 A1 | 1/2013 | Shavelsky et al. |
| 2016/0106625 A1 | 4/2016 | Dunleavy et al. |

\* cited by examiner

COMPLIANCE PILL TRAY SYSTEM

CROSS-REFERENCE TO RELATED APPLICATIONS

This application is a continuation-in-part to co-pending U.S. application Ser. No. 14/323,523 filed Jul. 3, 2014, and entitled "Compliance Pill Tray System."

This application is also a non-provisional to U.S. Provisional Application Ser. No. 62/328,883 filed Apr. 28, 2016, entitled "Color Coded Closure System & Pill Tray Dispenser for Enhancing Medication Compliance."

FIELD

This disclosure relates generally to a compliance system for a plurality of prescription medications. More particularly, this disclosure relates to a compliance system having a pill tray and dosage tables applied to the prescription container systems of the prescribed medications for the purpose for improving patient compliance in taking prescription medication by assisting the user in accurately dosing the pill tray.

BACKGROUND

Compliance in regards to the taking of prescription medication is the degree to which a patient correctly follows the doctor's directions in taking medication. One problem observed with the use of prescription medications is a low level of compliance by patients in taking the medications as directed. For example, in the case of the brief instructions "take one tablet per day," it has been observed that patients often do not take a tablet each day, or, if they do, the timing of the taking of the medication is not appropriately spaced. Appropriate spacing in this case would be one tablet every twenty-four hours. However, while a patient may typically take the tablet at the same time each day during the week, such as at 8 am, on the weekend, the patient may sleep later and be out of their weekday routine. This can result in the patient either forgetting to take the tablet or else taking it much later in the day. This undesired schedule for taking the medicine could have adverse effects to the patient. Also, it is not uncommon for a patient to take their medicine, but forget later whether or not they actually took their medicine. This is especially common if a patient is to take a medication several times per day and/or multiple medications per day, as increased medications and frequency of each medication represents increased opportunities to fail to comply or to forget whether or not they complied.

Various approaches have been taken in an effort to improve patient compliance in taking prescription medication. For example, U.S. Pat. No. 7,907,477 describes a timer to be applied to a cap for a prescription container for improving compliance. U.S. Pat. No. 5,014,798 describes a cap for a prescription container having a computer chip for monitoring of patient usage. U.S. Pat. No. 6,574,165 describes a pill dispenser having a timer configured to ring an alarm when a medication is to be taken. The various attempts to improve compliance such as the above have various disadvantages in terms of expense, complexity, and acceptability to the patient. For example, generally speaking, the persons who are most likely to need prescription medication and to be non-compliant are over the age of about fifty and, in many cases, are on fixed incomes or insurance plans that are limited in coverage. This group is generally less likely to adapt to compliance methods involving more complex and expensive technology.

Another approach, as disclosed in U.S. Patent Publication Nos. 2004/0188998 and 2008/0077439, is to provide the customer with a calendar in conjunction with a prescription where the calendar provides information as to when the patient should take a prescribed medication. As broadly disclosed in these references, the calendar could be applied as a label on the pharmaceutical container or provided as a separate sheet accompanying the prescription container. However, while offering a calendar is inexpensive to implement and generally easy to explain and use, the calendar systems disclosed in these references are ineffective for several reasons. In particular, as noted above, compliance issues are particularly common when multiple medications are prescribed, but the calendars disclosed in these applications are generally intended for only one medication dispensed in a standard prescription container. Thus, if a patient were prescribed multiple medications at one time, the patient would have to keep track of multiple calendars. Further, the calendars do not correspond particularly to the containers or otherwise leave sufficient space for standard prescription labels.

Accordingly, other approaches have been taken in an effort to improve compliance with respect to patient's that are prescribed multiple medications. Many of these approaches include dosing medications into a plurality of compartments corresponding to pre-assigned times to take the medications. For example, U.S. Pat. No. 5,159,451 describes a medicine reminder cabinet for dosing prescribed medications into separate compartments and including means for automatically dispensing the medications from the cabinet at appropriate times. Similarly, U.S. Pat. No. 5,826,217 describes a programmable medicine dispenser in which a medication administration schedule is programmed into the dispenser and a medication compartment is automatically opened upon acknowledgement of a user of an alarm instructing the user to take a scheduled dosage. Similar to the expense, complexity, and acceptability issues of the mechanical mechanisms described above with respect to singular prescriptions, patients are not likely to adapt to automated dispensers such as the above. Further, these types of machines often require complex counters and dispensing mechanisms that must be designed to accept and dispense differently sized and shaped pills. Such mechanisms often break down causing inaccurate dosing and/or broken or crushed medications. Additionally, such designs are generally bulky and lack portability, which is heavily desired in allowing the user to take their medications with them as they go about their daily routine.

In view of the above, traditional pill trays are still the most commonly used tool for compliance in taking multiple prescriptions because they are generally simple, portable, and inexpensive. Further, despite their simplicity, they are believed to be quite effective based, at least in large part, on the user going through the process of manually dosing the individual compartments. However, problems still persist with typical pill trays in that they must first be dosed accurately. Further, a user must still remember to take the appropriate doses at the appropriate times. In this respect, various approaches have been taken to improve traditional pill trays.

For example, U.S. Pat. No. 8,174,370 discloses an automated pill tray reminder device where each compartment of the pill tray includes an integrated light pipe that is selectively illuminated for alerting the user to consume a preselected dosage in the compartment. While the pill tray device of the '370 patent includes a cover for applying a plurality of separate labels "used to describe particular dosages," the labels do not correspond in any way to the compartments of the pill tray. In fact, the cover allows for placement of sixteen labels divided into two columns while the pill tray includes twenty-eight separate compartments divided into a table with seven columns and four rows. Further, each of the separate labels provided on the pill tray must still be matched with the correct prescription container system prior to dispensing the medications of the prescription container systems in the appropriate dosage compartments of the pill tray. In other words, the separate labels are merely redundant as a user would still have to refer to the prescription label of each prescription container to at least match the container with the appropriate label of the pill tray. More likely, the user will ignore the separate labels of the pill tray and refer only to the prescription label of each prescribed medication on the actual prescription container to dose the pill tray. Accordingly, the separate labels to be applied to the cover of the pill tray of the '370 patent do not effectively assist in dosing the pill tray.

U.S. Pat. No. 6,550,618 provides another improved pill tray in which an information card is secured to the pill tray. As shown in FIG. 2 of the '618 patent, each information card requires three critical elements: 1) a photograph of each medication to be taken by the patient; 2) for each medication, a weekly graphical representation of the medications as they should be dosed into the particular compartments of the pill tray; and 3) a duplicate of the prescription label that would, as required by law, already be included on the container in which the medication would have been dispensed. These elements are provided in a row format wherein each row includes information for only one of the medications. Accordingly, while the '618 patent provides information to assist in dosing the pill tray, the '618 patent, like the '370 patent described above, requires each prescription container system to still be matched with the appropriate medication information of the information card prior to dispensing the medications of the prescription container systems in the appropriate dosage compartments of the pill tray. Thus, as noted above with respect to the '370 patent, the information card of the '618 patent is redundant and, if a user actually uses the information card in dosing the pill tray, adds an unnecessary matching step, which only increases the chance of inaccurate dosing of the pill tray. Additionally, the information card of the '618 patent is extremely convoluted, particularly in cases where the patient is prescribed more than two or three medications. In fact, as pointed out in the background of the '618 patent, it is common for patients to be prescribed five or more medications. However, the figures depict at most four medications being able to be provided on a full sheet of paper, which then must be attached to the tray in an awkward and clumsy way. Thus, multiple information cards would be needed for more than a couple of medications unless the information is provided in very small print, which is obviously undesirable. Further, when the information card is provided in a more desirable position such as the inside surface of a cover for the pill tray as shown in FIG. 5, the information card must be even smaller, further reducing the number of medications that can be shown on one card. In summary, too much information on the information card as disclosed in the '618 patent is just as problematic as too little information.

U.S. Pat. No. 4,473,156 describes another compliance system in which each prescribed medication is transferred from original prescription containers to "interim" containers identified by particular colors indicating the times during which the pills in the container are to be dispensed into corresponding colored compartments of a pill tray. While the '156 patent does provide colors on a pill container corresponding to compartments of a pill tray, the compliance system of the '156 patent has many flaws. In particular, by transferring the medications from their original container to interim containers, each medication is separated from the critical information of the prescription label provided by the pharmacy prior to being dispensed into a pill tray. Similarly, a pharmacy cannot perform the transfer because they are required to dispense prescribed medications in containers containing traditional prescription labels. Thus, the containers and trays of the '156 patent are intended to be used by staff of a medical facility, such as nursing homes, after receiving each of a patient's prescribed medications.

Further, as each interim container in which a prescribed medication is dispensed includes only those colors in which the prescribed medication is to be taken, the system of the '156 patent requires the medical facility to store a number of different containers each marked with different potential color variations. Only including the colors in which the prescribed medication in the interim container is to be taken also prevents a consistent graphical representation on the interim containers of the dosage compartments of the pill tray. In other words, while the '156 patent teaches using colors on pill containers to identify dosage compartments in which medications in the pill containers are to be dispensed, there is no consistent order/sequence of the identifying colors on the containers of the '156 patent because each container includes only the colors identifying the times in which the prescribed medication in the container is to be taken. It is also noted that the compliance system of the '156 patent provides no ability to identify medications for the inevitable situation in which at least one of the prescribed medications is to be taken more than once during a particular dosage interval. Thus, a user must still keep or otherwise refer to the prescription label of the original container when distributing the prescribed medications into the appropriate compartments of the pill tray to determine how many pills of each medication are to be taken during each dosage interval.

In summary, the extra step of transferring prescribed medications from their original containers to interim containers containing the assigned colors prior to dispensing the medication into appropriate compartments as provided in the '156 patent is plagued with deficiencies that significantly increase the likelihood of mistakes in accurate dosing of the pill tray, not to mention the additional time, expense, and frustration of requiring the user to transfer each medication from its original container to interim containers having appropriately assigned colors prior to dispensing the medications to the pill tray.

Solving the above and other needs, the present disclosure provides a compliance system that is inexpensive to implement and promotes continuous and consistent compliance of multiple medications using a pill tray.

SUMMARY

The disclosure advantageously provides a prescription compliance system for improving patient compliance in taking a plurality of prescribed medications where each of the plurality of prescribed medications are to be housed in one of a plurality of prescription container systems and each having dosing instructions providing that the prescribed medication is to be taken according to a sequence schedule. The prescription compliance system includes a pill tray and a prescription container labeling system. The pill tray includes at least one frequency section and a plurality of sequence compartments within each frequency section, the plurality of sequence compartments configured for receiving the plurality of prescribed medications according to the sequence schedule of each of the plurality of prescribed medications. The prescription container labeling system includes a plurality of dosage tables each configured to be applied to one of the prescription container systems, each dosage table including a plurality of demarcated sequence sections sequentially aligned with the plurality of sequence compartments of the at least one frequency section of the pill tray and each of the demarcated sequence sections configured to receive a dosage number identifying how many pills of the prescribed medication in the container system to which the dosage table is applied should be dosed to the corresponding sequence compartment of the at least one frequency section of the pill tray to provide graphical dosage instruction information for the patient in dosing each of the sequence compartments of the pill tray with each of the plurality of prescribed medications.

According to certain embodiments, the prescription container labeling system includes a plurality of blank prescription labels for subsequent printing of prescription specific information at a dispensing entity, each of the blank prescription labels including one of the plurality of dosage tables printed thereon without dosage numbers in the plurality of demarcated sequence sections such that the dosage tables are configured to receive the dosage numbers at the dispensing entity.

According to certain embodiments, the prescription container labeling system includes a roll of blank prescription labels for subsequent printing of prescription specific information at a dispensing entity, each blank prescription label including a first distinct section for printing of traditional prescription information and a second distinct section including one of the plurality of dosage tables. According to some embodiments, the first distinct section of each blank prescription label is separated from the second distinct section by a perforated line such that the first and second distinct sections are operable to be applied together to one of the prescription container systems or the second distinct section may be removed from the first distinct section.

According to certain embodiments, the prescription container labeling system includes a plurality of stickers for distribution to a dispensing entity, each of the plurality of stickers including one of the plurality of dosage tables printed thereon and dosage numbers printed in the plurality of demarcated sequence sections of each dosage table according to potential sequence schedules for the plurality of prescribed medications.

According to certain embodiments, the prescription container labeling system includes a plurality of stickers for distribution to a dispensing entity, each of the plurality of stickers including one of the plurality of dosage tables printed thereon without dosage numbers printed in the plurality of demarcated sequence sections such that the dosage tables of the stickers are configured to receive handwritten dosage numbers at the dispensing entity.

According to certain embodiments, the dosage tables are applied to a closure of the prescription container system. According to some embodiments, the dosage tables are disposed on a liner inserted into a cavity of the closure. According to some embodiments, dosage tables are distributed to a dispensing entity without dosage numbers printed in the plurality of demarcated sequence sections such that the dosage tables are configured to receive handwritten dosage numbers at the dispensing entity. According to some embodiments, the prescription container labeling system further comprises a second dosage table applied to a container of the container system, the dosage numbers of the second dosage table matching the dosage numbers of the dosage table applied to the closure.

According to certain embodiments, each of the sequence compartments of one of the frequency sections of the pill tray are assigned sequence identifiers in assigned colors and each of the demarcated sequence sections of the dosage tables include colored sequence identifiers matching the sequence identifiers of the corresponding sequence compartments of the pill tray.

According to another embodiment of the disclosure, a method is provided for improving patient compliance in taking a plurality of prescribed medications each having prescription instructions providing that the prescribed medication is to be taken each day according to a sequence schedule. The method includes providing a pill tray to a patient including at least one frequency section and a plurality of sequence compartments within each frequency section, the plurality of sequence compartments configured for receiving the plurality of prescribed medications according to the sequence schedule of each of the plurality of prescribed medications; and dispensing each of the plurality of prescribed medications to the patient in a prescription container system, the dispensing step including, for each prescribed medication, applying a dosage table to the prescription container system in which the prescribed medication is dispensed, the dosage table including a plurality of demarcated sequence sections sequentially aligned with the plurality of sequence compartments of the at least one frequency section of the pill tray and each of the demarcated sequence sections including a dosage number identifying how many pills of the prescribed medication should be dosed to the corresponding sequence compartments of the pill tray. The dosage tables for each prescribed medication provide graphical dosage instruction information for the patient in dosing each of the sequence compartments of the pill tray according to the sequence schedules of each of the plurality of prescribed medications.

According to certain embodiments, the method further includes receiving from a label supplier a plurality of blank prescription labels for subsequent printing of prescription specific information at a dispensing entity, each of the blank prescription labels including the dosage table printed thereon without dosage numbers in the plurality of demarcated sequence sections such that the dispensing step further includes providing the dosage numbers to the dosage table. According to some embodiments, the dosage numbers are printed in the plurality of demarcated sequence sections with the prescription specific information based on prescription information entered into a pharmacy computer.

According to certain embodiments, the method further includes receiving from a label supplier a roll of blank prescription labels for subsequent printing of prescription specific information at a dispensing entity, each blank prescription label including a first distinct section for printing of traditional prescription information and a second distinct section including the dosage table to be applied to one of the prescription container systems. According to some embodiments, first distinct section of each blank prescription label is separated from the second distinct section by a perforated line such that the first and second distinct sections are operable to be applied together to one of the prescription container systems or the second distinct section may be removed from the first distinct section.

According to certain embodiments, the method further includes receiving from a label supplier a plurality of stickers, each of the plurality of stickers including one of the dosage tables printed thereon and dosage numbers printed in the plurality of demarcated sequence sections of each dosage table according to potential sequence schedules for the plurality of prescribed medications, the dispensing step including choosing one sticker from the plurality of stickers for application to the prescription container system according to the dosage schedule of the prescribed medication being dispensed and the dosage numbers of the stickers.

According to certain embodiments, the method further includes receiving from a label supplier a plurality of stickers, each of the plurality of stickers including one of the plurality of dosage tables printed thereon without dosage numbers printed in the plurality of demarcated sequence sections, the dispensing step further including handwriting of the dosage numbers in the dosage tables.

According to certain embodiments, for each prescribed medication, the dosage table is applied to a container of the container system and the dispensing step further includes applying a closure to the container, the closure including a second dosage table matching the dosage table applied to the container to which the closure is applied. According to some embodiments, the dispensing step further includes, for each prescribed medication, handwriting dosage numbers on the dosage table of the closure that match the dosage numbers of dosage table applied to the container to which the closure is applied.

According to certain embodiments, each of the sequence compartments of one of the frequency sections of the pill tray are assigned sequence identifiers in assigned colors and each of the demarcated sequence sections of the dosage tables include colored sequence identifiers matching the sequence identifiers of the corresponding sequence compartments of the pill tray.

BRIEF DESCRIPTION OF THE DRAWINGS

Further advantages of the disclosure are apparent by reference to the detailed description in conjunction with the figures, wherein elements are not to scale so as to more clearly show the details, wherein like reference numbers indicate like elements throughout the several views, and wherein.

DETAILED DESCRIPTION

The present disclosure provides a prescription compliance system that utilizes a pill tray and a corresponding prescription container labeling system for providing graphical dosage instruction information for the patient in dosing the pill tray. While the compliance system may be utilized for singular prescriptions, it is particularly useful when a patient is prescribed multiple medications taken in various dosages at specified times/sequences during the day. In this regard, as most patients take the same prescribed medications each day according to the same schedule, the compliance system assigns various dosage times in which a patient may be instructed to take prescribed medications a particular sequence identifier (e.g., indicia such as "morning" and "evening", symbols such as a rooster and moon, etc.). Each sequence identifier is preferably further assigned a particular color. Each sequence identifier and corresponding color then remain consistent in the various components of the compliance system as described below to provide an intuitive approach for accurately dosing the pill tray with the plurality of prescribed medications, and, thus, improved compliance in taking the prescribed medications.

Figure 1A:
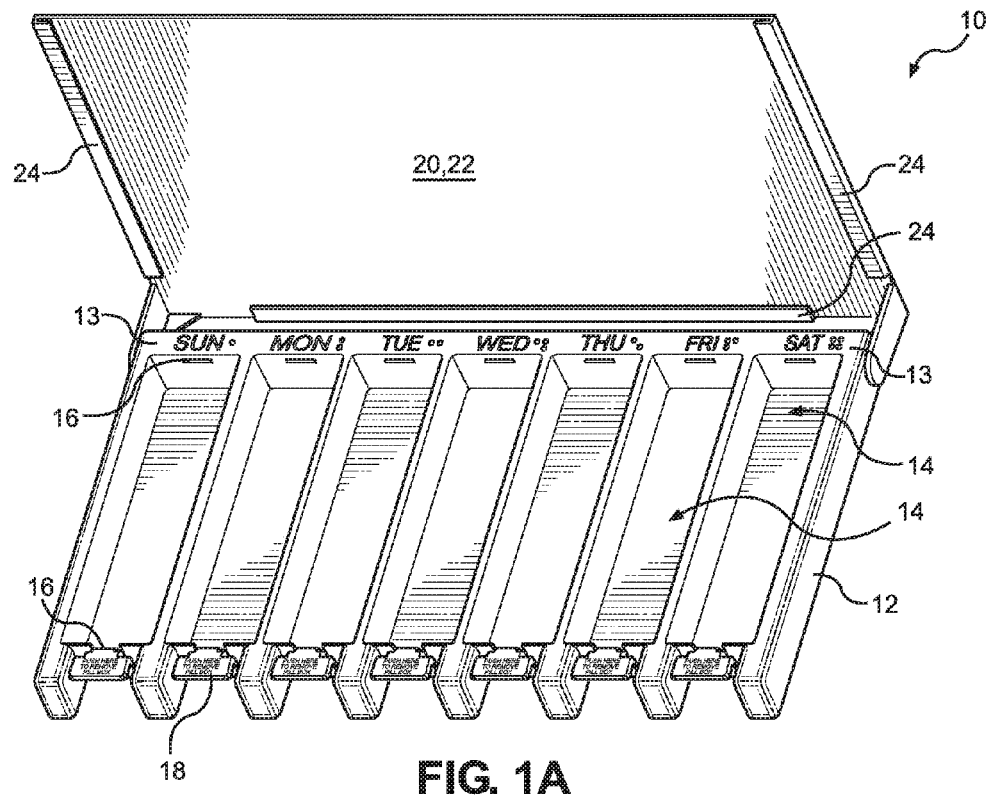
FIGS. 1A-1B depict a perspective view of a pill tray having removable frequency sections according to one embodiment of the present disclosure.
Figure 1B:
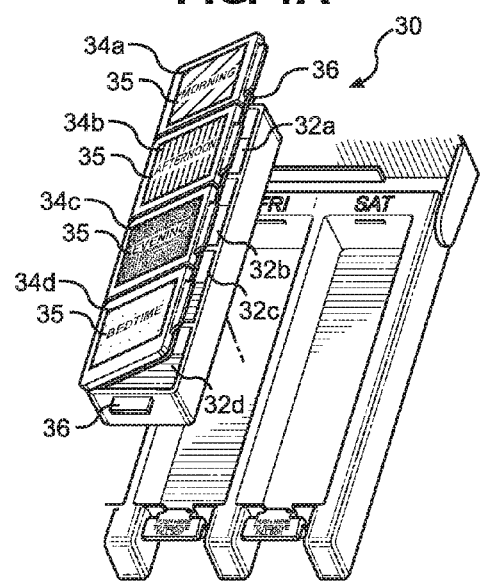
Figure 2:
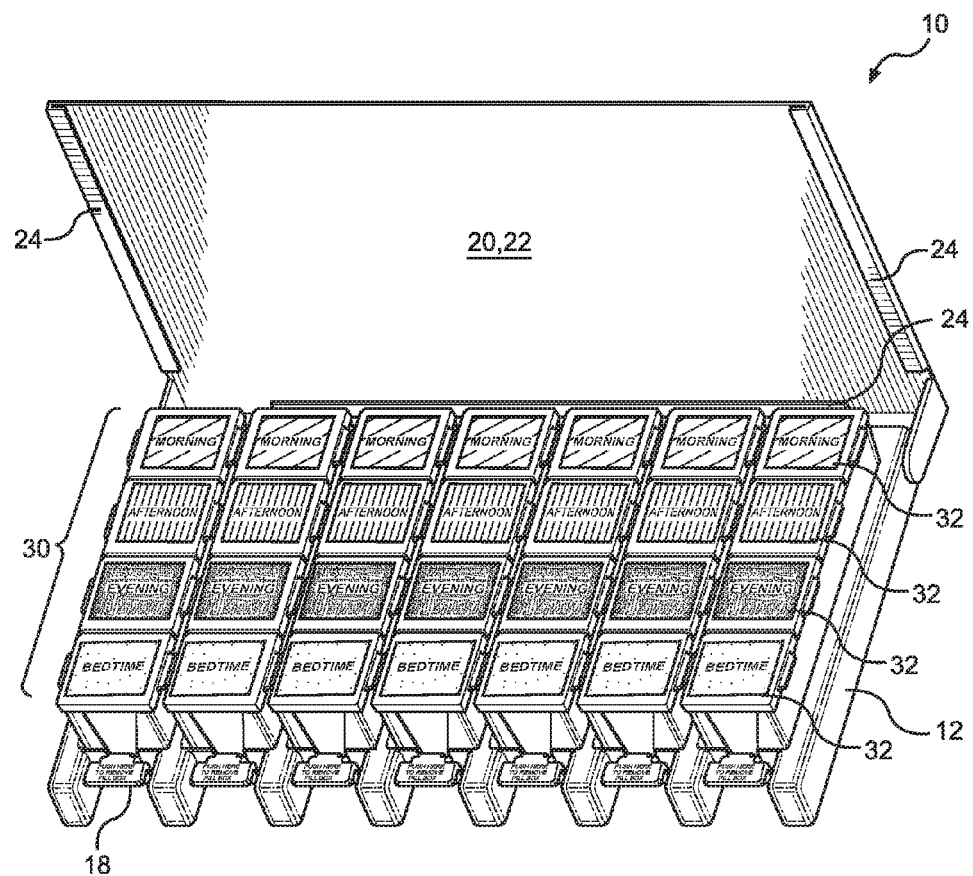
FIG. 2 depicts a perspective view of the pill tray of FIGS. 1A-1B with the removable frequency sections secured to the pill tray according to one embodiment of the disclosure.

With initial reference to FIGS. 1A-1B and FIG. 2, there is shown a pill tray 10 preferably having three main components: a base portion 12, a cover 20, and a plurality of removable pill tray sections 30. The base portion 12 includes a plurality of cavities 14 for receiving the pill tray sections 30. Each cavity 14 includes engaging mechanisms 16 that correspond to engaging mechanisms 36 of the pill tray sections 30 such that the sections 30 may be secured to the appropriate cavity 14 of the base portion 12. As shown, the cavity engaging mechanisms 16 are preferably slots and the pill tray section engaging mechanisms 36 are preferably tab elements sized and configured to engage the slots 16. To assist a user in removing the sections 30, each cavity 14 is preferably provided with a release tab 18 for pushing the section tab elements 36 out of the slots 16. The pill tray sections 30 are preferably removable to provide additional convenience in going about the patient's daily affairs. In other words, if desired, the patient can remove a pill tray section 30 corresponding to one day of prescribed medications to take with the patient as the patient goes about their day.

In preferred embodiments, the pill tray 10 is a weekly pill tray and the base portion 12 is configured to receive seven separate daily pill tray sections 30. Further, referring particularly to FIG. 1B, each daily section 30 is further separated into a plurality of sequence compartments 32 corresponding to the different times the user takes their prescribed medications during the day. As shown, the daily section 30 of the preferred embodiment is divided into four sequence compartments 32a-32d corresponding to four sequence identifiers such as MORNING (or MORN for short), AFTERNOON (or NOON for short), EVENING (or EVE for short), and BEDTIME (or BED for short). Each sequence compartment 32a-32d includes a lid 34a-34d preferably hingedly connected to the sequence compartments 32a-32d for opening and closing the particular sequence compartment 32. Each lid 34a-34d preferably includes indicia 35 corresponding to the sequence identifier assigned to the sequence compartment 32a-32d. Further, each sequence identifier is preferably assigned a distinct color such as MORNING in blue, AFTERNOON in red, EVENING in black, and BEDTIME in green. The indicia 35 is preferably provided using appropriate stickers placed on the lids of the compartments. However, the indicia 35 of each sequence compartment may also be imprinted, embossed, or molded with the appropriate identifier and/or appropriate color. Alternately, the individual compartments of a particular sequence are molded together as the same color (such as in embodiments in which the daily sections are not removable) and/or each row includes the appropriate sequence identifier before and/or after the row.

While the pill tray 10 is shown and described above as a weekly pill tray for receiving seven removable daily sections 30, it should be understood that the tray 10 could be configured to receive or otherwise include any number of sections 30 as desired. Further, the sections 30 may also correspond to other frequencies in which prescribed medications are to be taken such as every twelve hours, two days, weekly, etc. Accordingly, while the term "daily sections" is generally used in describing preferred embodiments of the disclosure, the daily pill tray sections 30 may be more broadly referred to herein as "frequency sections," with the sequence compartments 32 of the frequency sections 30 then corresponding to particular times the prescribed medications may be taken during each frequency.

In preferred embodiments, the pill tray 10 includes a cover 20 connected to the base portion 12 such that it is operable to move from an open position (FIG. 2) to a closed position (FIG. 11). As shown, the cover 20 is preferably hingedly connected to a top end 13 of the base portion 12 such that an inside surface 22 of the cover 20 is visible when the cover 20 is in the open position. In this embodiment, the inside surface 22 of the cover 20 further includes one or more slots 24 for removably receiving a compliance sheet that is visible to the user when the cover 20 is in the open position. In preferred embodiments, the compliance sheet inserted into the slots 24 of the cover 20 provides instructions to the user in dosing the sequence compartments 32 of the pill tray 10 using the dosage tables of the container systems as described above. The compliance sheet and/or cover may also be used to provide prescription information to the user such as by displaying dosage tables to the user for each prescribed medication. When the cover 20 is moved to the closed position, the cover 20 assists in preventing the frequency sections from popping out of the base portion 12 and/or the lids 34 of the sequence compartments 32 from unintentionally opening. In the closed position, promotional information is preferably displayed to the user on the cover 20 of the pill tray 10.

It should be understood that other configurations for the pill tray 10 and/or cover 20 are possible and within the scope of the present disclosure so long as the tray 10 includes at least one frequency section and a plurality of sequence compartments within the frequency section. Further, in embodiments of the pill tray 10 that include a cover 20, information sheets could be secured to the cover 20 in a number of alternative ways such as clips, magnets, adhesive, etc. In preferred embodiments, however, the attachment mechanisms for securing the information sheet to the cover 20 permit the sheet to be easily removed from the cover 20 and replaced with a new information sheet as desired.

Figure 3A:
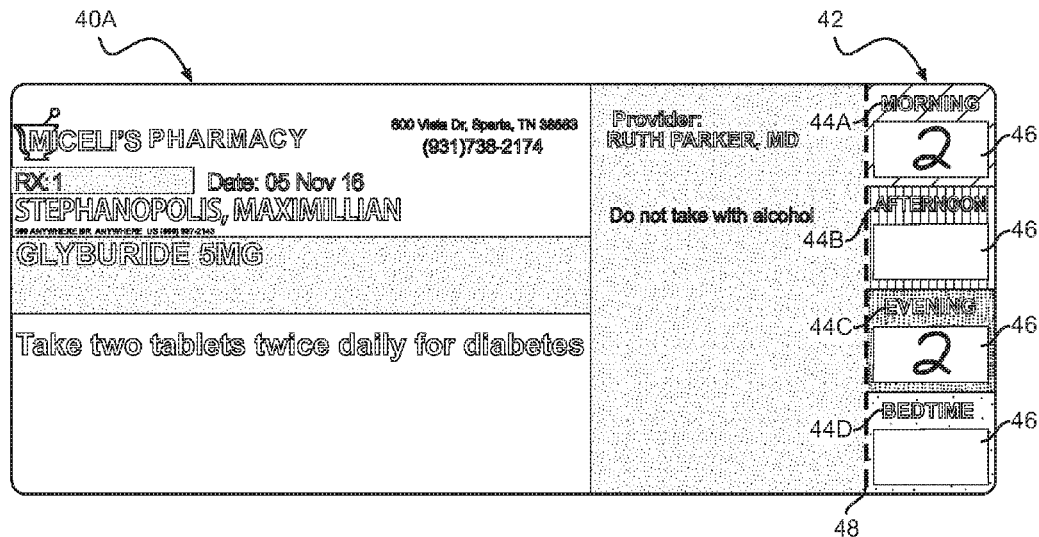
FIG. 3A depicts an exemplary glyburide prescription label having a dosage table for a container according to one embodiment of the disclosure.
Figure 3B:
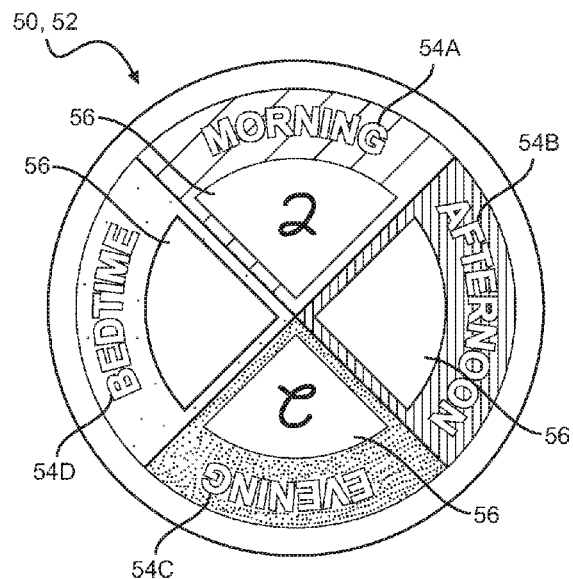
FIG. 3B depicts a liner having a dosage table corresponding to the glyburide prescription of FIG. 3A to be applied to a closure according to one embodiment of the disclosure.
Figure 3C:
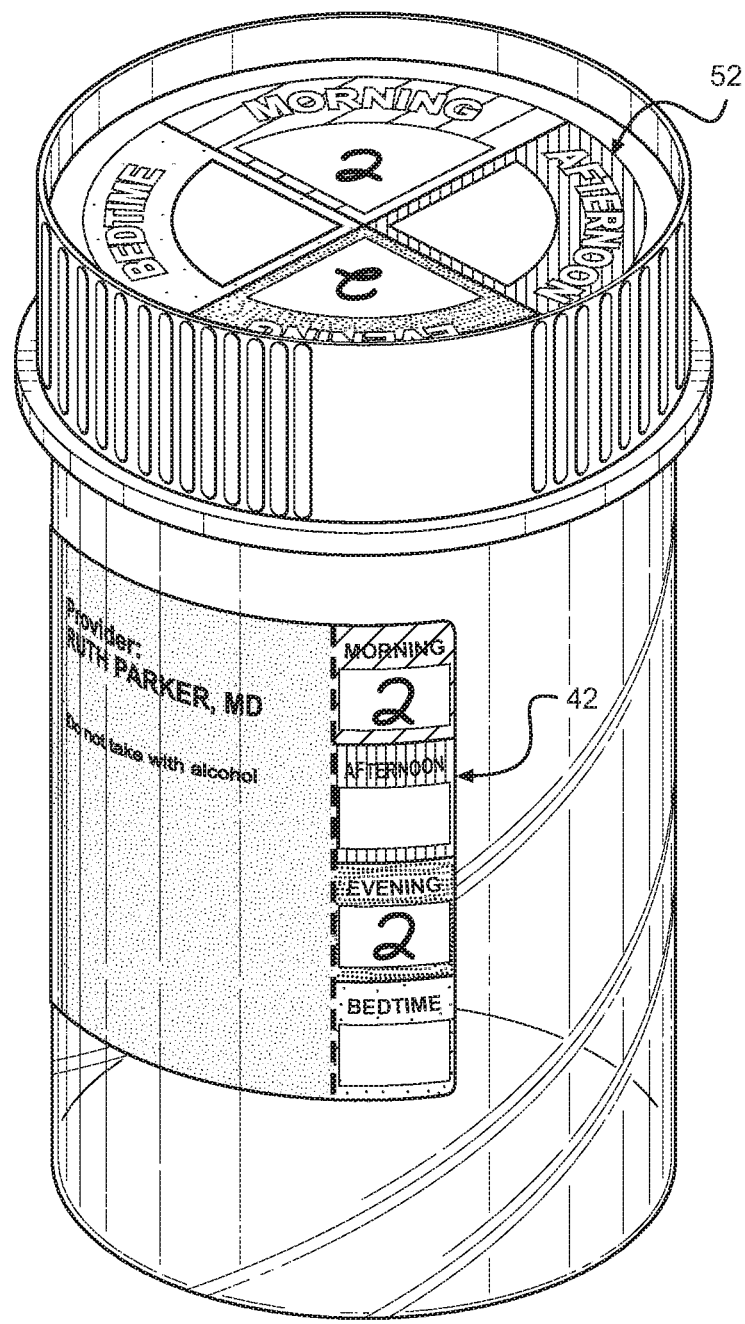
FIG. 3C depicts the prescription label of FIG. 3A and the liner of FIG. 3B applied to a container system according to one embodiment of the disclosure.
Figure 4A:
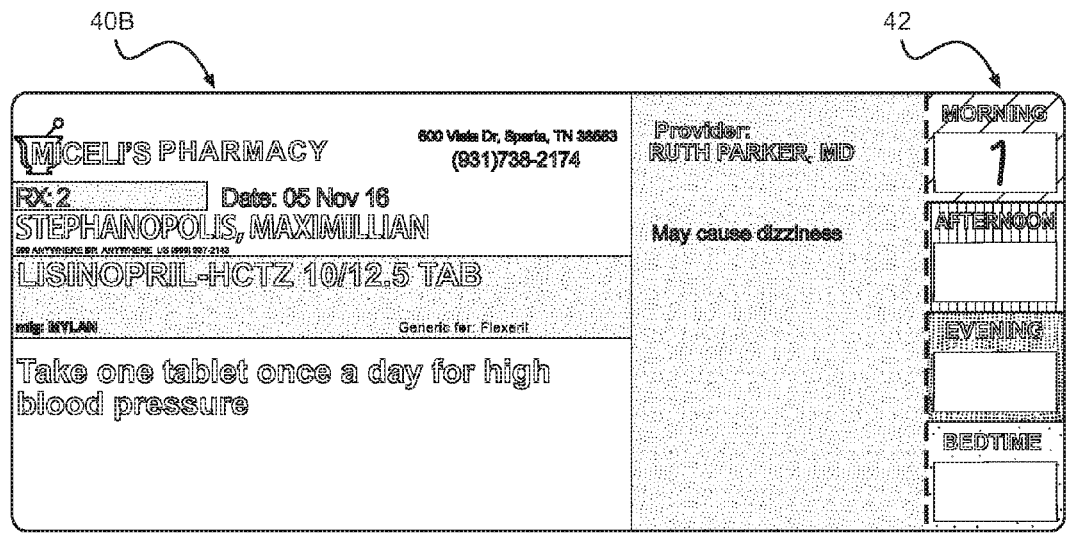
FIGS. 4A-4C depict the prescription label and liner of FIGS. 3A-3C for an exemplary lisinopril prescription according to one embodiment of the disclosure.
Figure 4B:
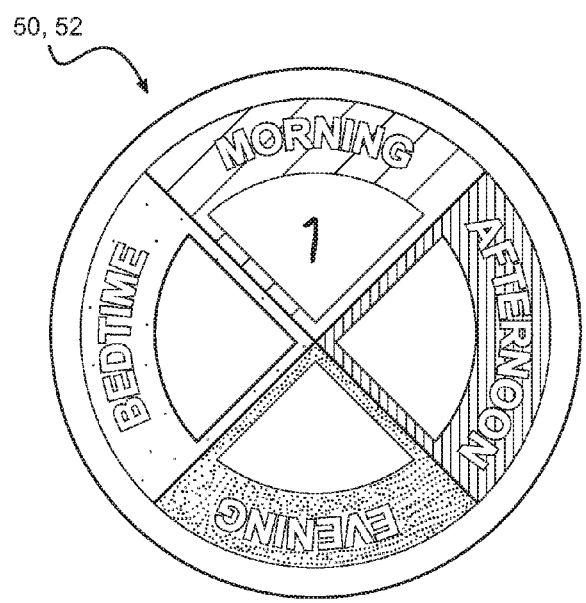
Figure 4C:
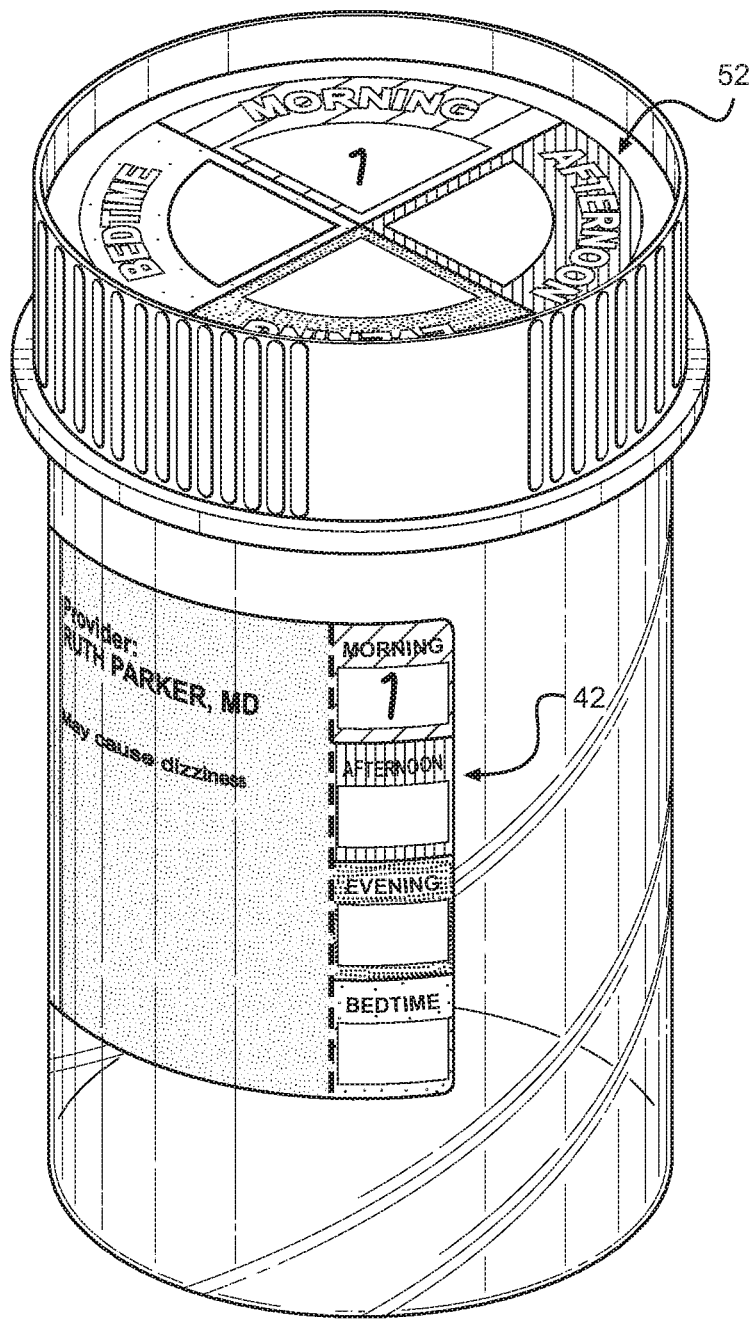
Figure 5A:
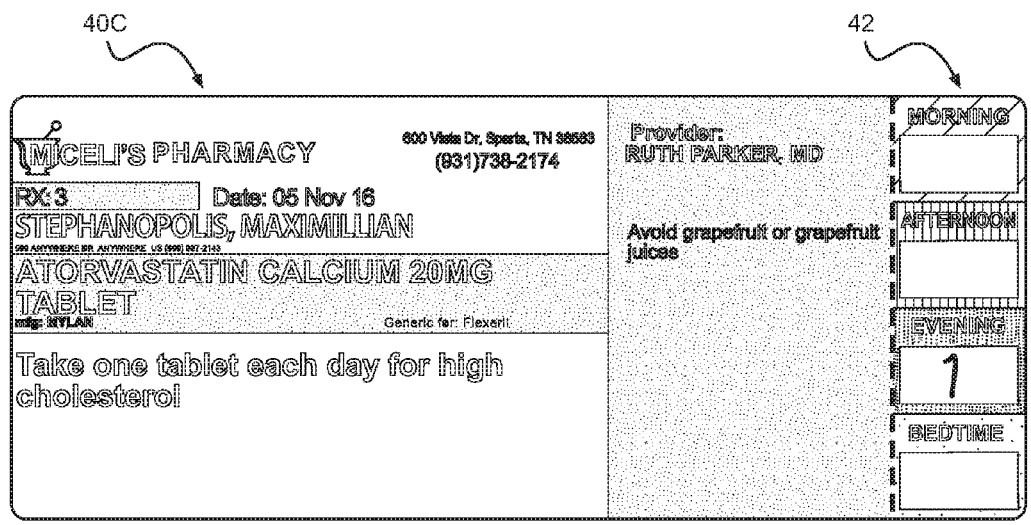
FIGS. 5A-5C depict the prescription label and liner of FIGS. 3A-3C for an exemplary atorvastatin prescription according to one embodiment of the disclosure.
Figure 5B:
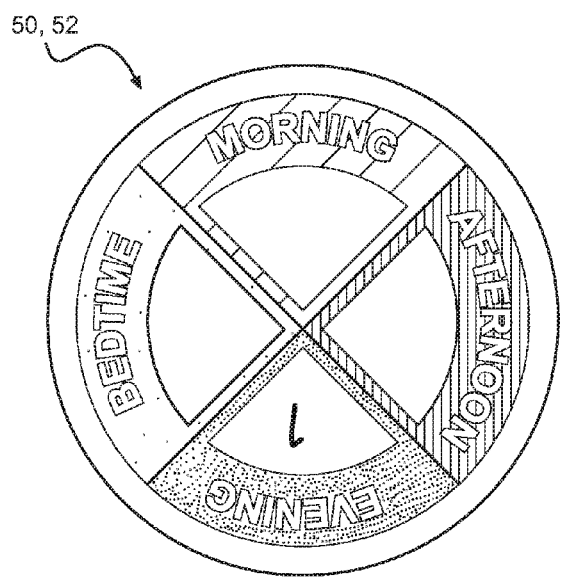
Figure 5C:
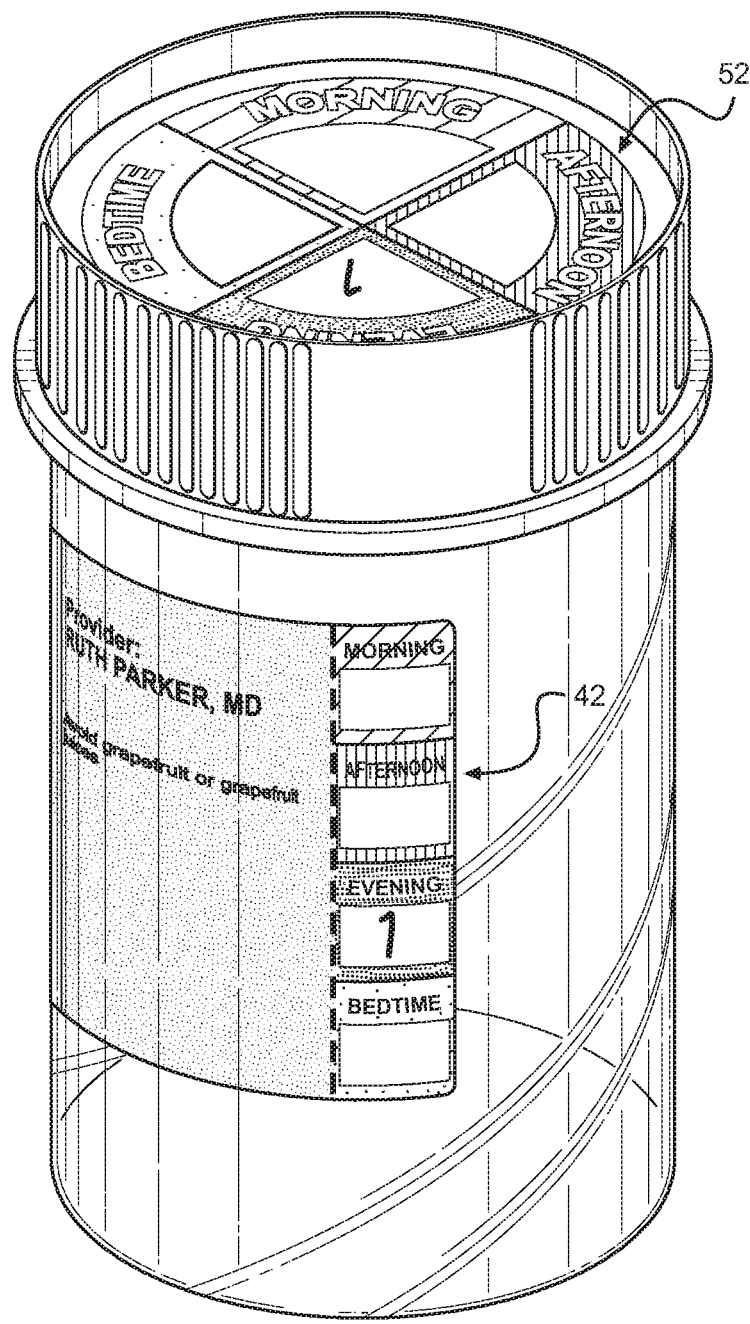
Figure 6A:
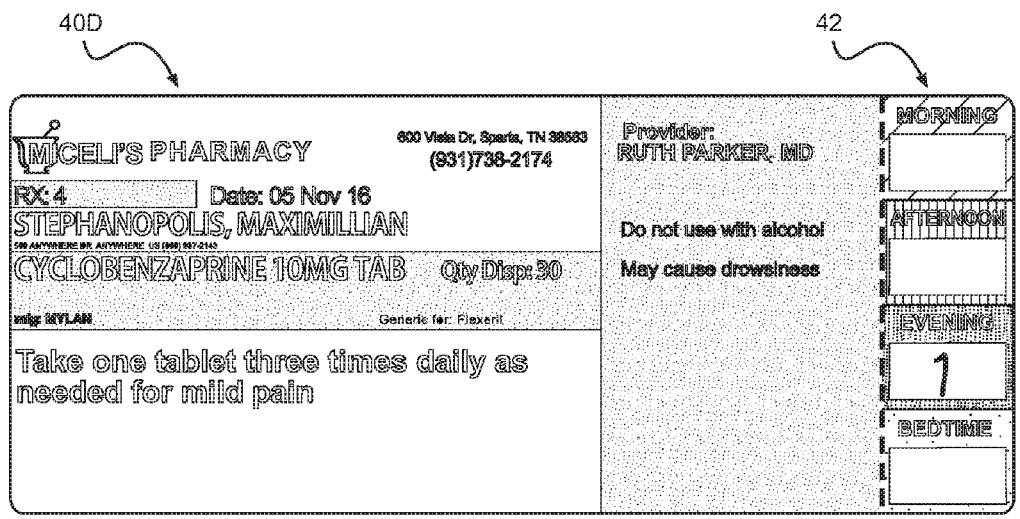
FIGS. 6A-6C depict the prescription label and liner of FIGS. 3A-3C for an exemplary cyclobenzaprine prescription according to one embodiment of the disclosure.
Figure 6B:
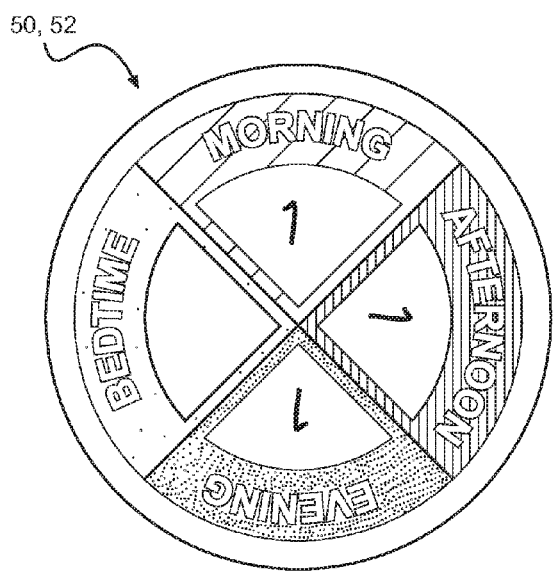
Figure 6C:
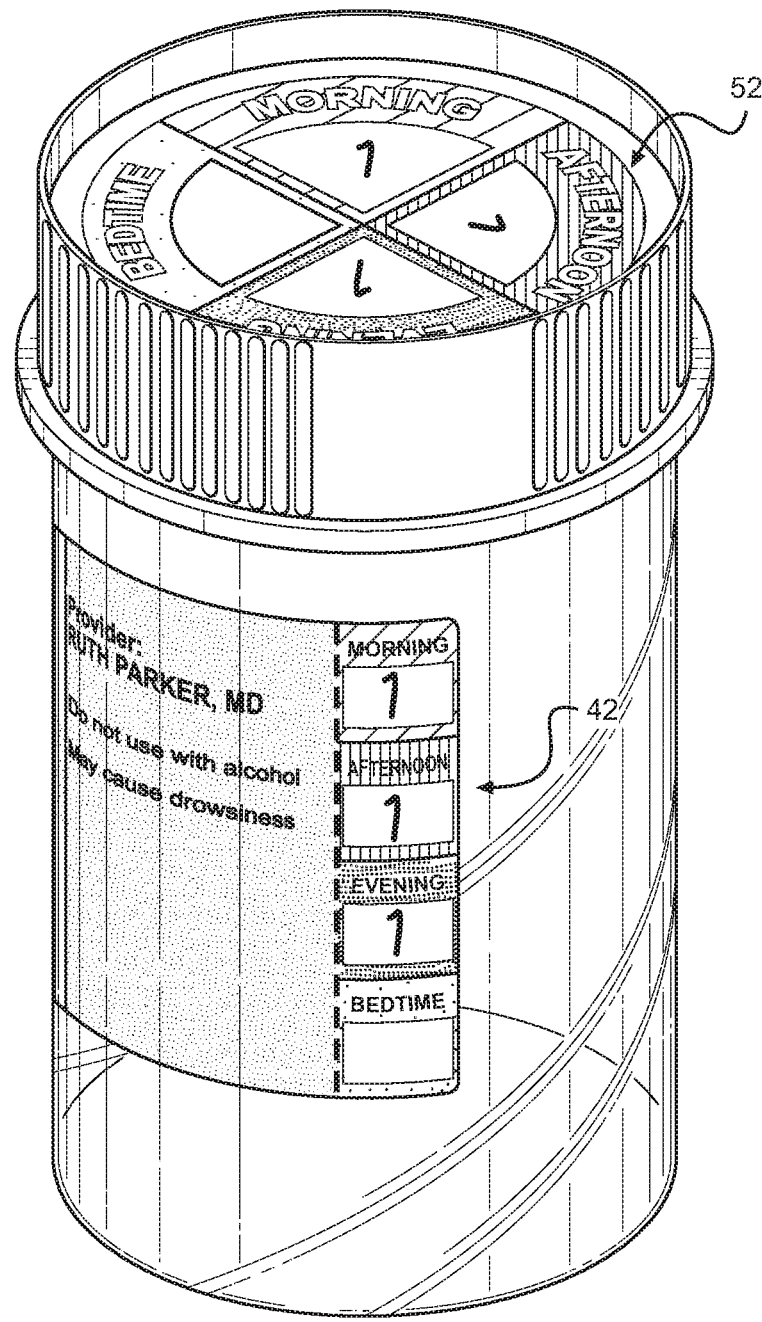

Referring to the exemplary "glyburide" prescription of FIGS. 3A-3C, the prescription compliance system of the present disclosure further includes a prescription labeling system for each prescribed medication that assists a user in accurately dosing each of a plurality of prescribed medications into the sequence compartments 32 of the pill tray 10 according to each prescribed medication's dosing schedule. In this regard, each prescription is dispensed with a dosage table 42 and/or 52 having simplified dosage information to be applied to a container system for each prescription dispensed by the pharmacy. While the dosage table is preferably provided on a label or sticker intended to be applied to a prescription container (as exemplified by FIG. 3A with label 40 having dosage table 42) and the closure for the container (as exemplified by FIG. 3B with liner 50 having dosage table 52) as shown and described herein, the dosage table may also be applied to just the container or just the closure. For purposes herein, a "container system" refers broadly to include both a container and a closure, while "container" and "closure" refer to these individual components of the "container system."

Figure 7A:
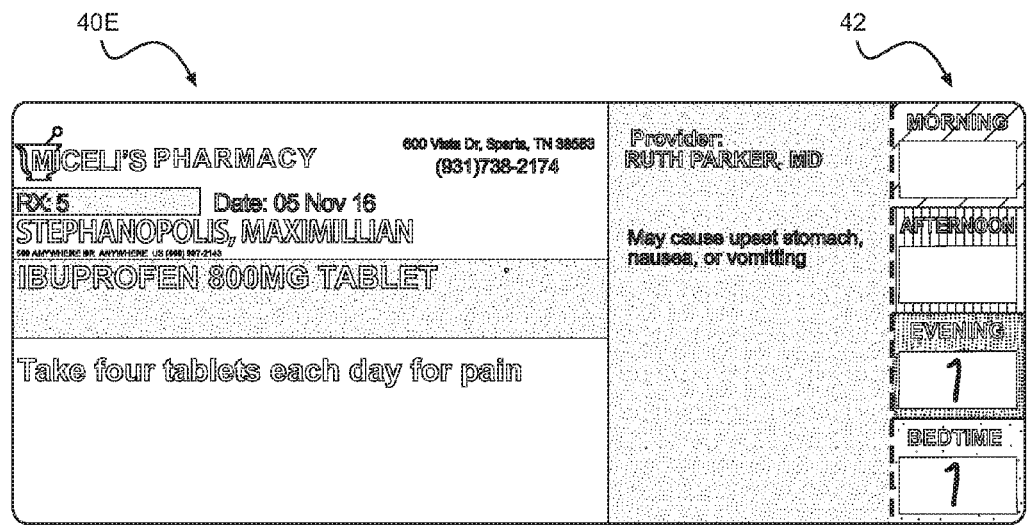
FIG. 7A-7C depict the prescription label and liner of FIGS. 3A-3C for an exemplary ibuprofen prescription.
Figure 7B:
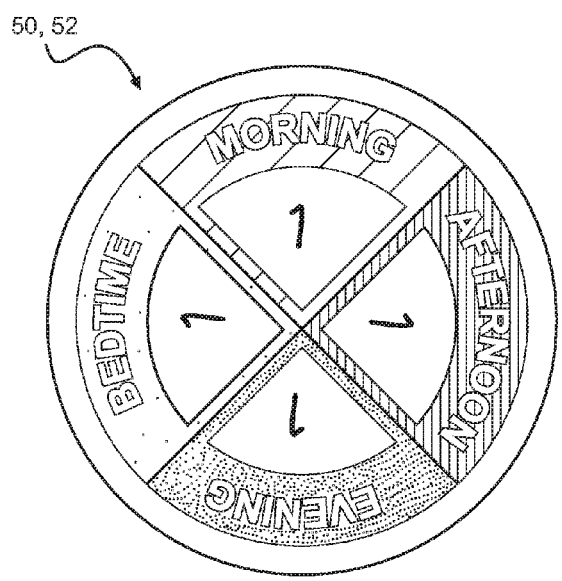
Figure 7C:
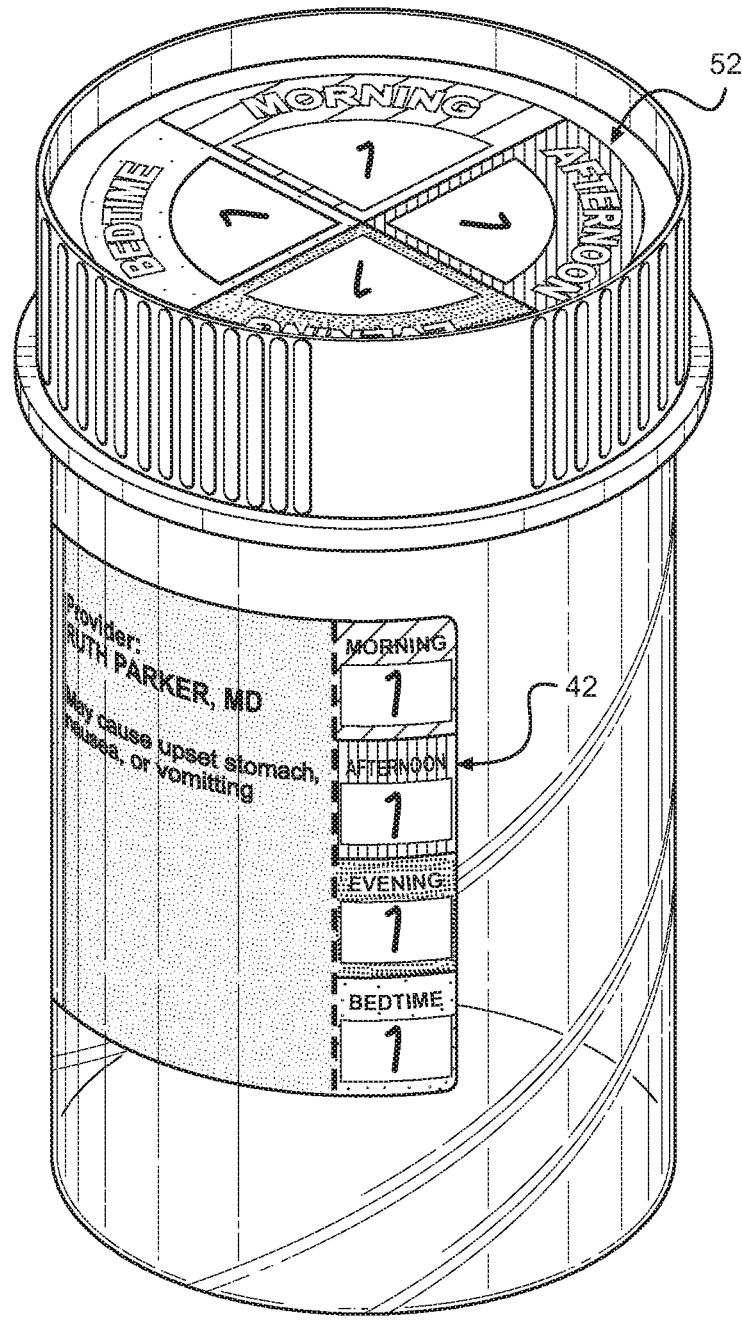

As shown, the simplified dosage information of each dosage table 42, 52 includes a demarcated sequence section 44, 54 for each sequence identifier (i.e., four demarcated sequence sections 44A-44D, 54A-54D in the example of the present disclosure corresponding to the MORNING, AFTERNOON, EVENING, and BEDTIME sequence compartments 32a-32d of pill tray 10) and, for each demarcated sequence section 44, 54, a dosage number 46, 56 indicating how many, if any, pills of the prescribed medication in the container system to which the dosage table 42, 52 is applied are to be taken during the sequence. Thus, according to an important aspect of the present disclosure, dosage tables 42, 52 provide a mechanism in which the dispensing entity converts more complicated traditional dosing instructions from a pharmacist into simplified dosing instructions identifying precisely how many pills of a particular medication are taken at a particular time of day. For example, referring to the ibuprofen prescription of FIG. 7A, prescribed dosing instructions from the doctor such as "take four tablets each day for pain" must be converted by the pharmacist to simplified instructions that are harmonious with the dosage tables 42, 52 of the present compliance system. According to this example, the pharmacist converted the prescribing doctor's dosing instructions to one pill during each sequence, which prevent users from taking too much of this particular medication at the same time.

When the prescribed medication is not to be taken during a particular sequence, the section corresponding to the omitted sequence is preferably left blank as shown. For purposes of the present disclosure, a sequence section 44, 54 is considered as including a dosage number 46, 56 whether left blank or including an actual "0" numeral so long as the other sequence sections 44, 54 of dosage table 42, 52 include dosage numbers 46, 56 greater than "0" where appropriate. According to preferred embodiments utilizing assigned colors for the sequence identifiers, at least some portion of each sequence section 44, 54 are provided in the same color as the corresponding sequence identifiers of sequence compartments 32 to further assist a user in matching the dosage numbers 46, 56 with the appropriate sequence compartments 32 of the pill tray 10.

As most prescriptions include dosing instructions that remain the same each day so long as the medication is prescribed to be taken, the demarcated sequence sections 44, 54 of dosage table 42, 52 are preferably in a format that graphically represents the sequence compartments 32 of one frequency section 30 of pill tray 10. For example, with respect to the pill tray 10 of FIGS. 1-2 having daily sections 30 each having four sequence compartments 32, each dosage table 42, 52 includes four sequence sections 44, 54 "arranged sequentially" with the corresponding MORNING, AFTERNOON, EVENING, and BEDTIME sequence compartments 32 of pill tray 10. It should be understood that "arranged sequentially" refers to the sequence sections 44, 54 of the dosage table 42, 52 being in the same sequential order as the corresponding sequence compartments 32 of the pill tray 10 to provide a graphical representation of one frequency section 30 of pill tray 10. In other words, using the present example of FIGS. 3A and 3B, the MORNING sequence section 44A, 54A is the first sequence section of each dosage table 42, 52 to correspond with the MORNING sequence compartment 32a being the first sequence compartment of each daily section 30 of pill tray 10, the AFTERNOON sequence section 44B, 54B is the second sequence section to correspond with the AFTERNOON sequence compartment 32b, the EVENING sequence section 44C, 54C is the third sequence section to correspond with the EVENING sequence compartment 32c, and the BEDTIME sequence section 44D, 54D is the fourth sequence section to correspond with the BEDTIME sequence compartment 32d. Further, it should be understood that dosage table 42, 52 graphically represents and is arranged sequentially with a pill tray daily section 30 when the sequence sections 52 are arranged vertically (as shown in FIG. 3A), horizontally (not shown), or in a clockwise circular fashion (as shown in FIG. 3B) regardless of the arrangement of the sequence compartments 32 of pill tray 10 so long as the sequence sections 44, 54 are in the same order as the corresponding sequence compartments 32.

In summary, each prescribed medication is dispensed by the dispensing entity in a container system including a dosage table 42, 52 that is preferably printed with dosage numbers 46, 56 for each potential sequence section 44, 54, and each sequence section 44, 54 is identified with the same color as the sequence compartments 32 to which the sequence section 44, 54 corresponds. By always including each of the sequence sections 44, 54, in the dosage tables 42, 52, each container system always provides a graphic representation of the sequences in which the patient is to take the medication and the number of pills to take during each sequence (i.e., a graphic representation of one frequency section 30 of the pill tray 10). This graphic representation allows the dispensing entity to continually educate and reinforce to the patient to follow the simplified dosing instructions of the dosage tables 42, 52 when dosing the pill tray, or when no pill tray is used, when taking the medication during a particular sequence of the day.

In comparison, U.S. Pat. No. 4,473,156 requires prescribed medications to be transferred from their original containers to interim containers as described in the Background section herein. Thus, the prescription labeling system of the present disclosure, which allows the pharmacy itself to put simplified dosage instructions directly on the container system housing the prescribed medication at the time the prescribed medication is dispensed, is a significant time saver as compared to the system of the '156 patent as it eliminates the interim containers. Further, the interim containers of the compliance system of the '156 patent simply provide colored stripes indicating the time of day in which the medication in the container is to be taken or dispensed in the pill tray. By omitting times of days in which the prescribed medication is not to be taken, the interim containers of the '156 patent do not provide a graphical representation of a pill tray. Further, by omitting dosage numbers, a user would still have to refer to the standard dosing instructions of the original prescription container.

In preferred embodiments, and as shown in FIGS. 3A, 4A, 5A, 6A, and 7A showing prescription labels 40A, 40B, 40C, 40D, and 40C for five prescribed medications of an exemplary Med-Sync program, the dosage tables 42 are preferably provided directly on or otherwise attached to the prescription labels in conjunction with typical prescription information such as the name of the patient, identification of the prescribed medication, full dosage instructions, etc. Referring to the exemplary "glyburide" prescription label 40A of FIG. 3A, which is applied to a prescription container as shown in FIG. 3C, dosage table 42 includes a MORNING demarcated sequence section 44A with the number "2" printed therein and an EVENING sequence section 44C with the number "2" printed therein because the dosage instructions for the glyburide prescription is "Take two tablets twice daily for diabetes." The AFTERNOON sequence section 44B and BEDTIME sequence section 44D are then left empty because the prescription is only prescribed to be taken twice daily. Similarly, the "lisinopril-hctz" prescription label 40B of FIG. 4A includes dosage table 42 with only the number "1" in the MORNING sequence section 44 because the dosage instructions for this prescription is "Take one tablet once a day for high blood pressure." The "atorvastatin calcium" prescription label 40C of FIG. 5A includes dosage table 42 with only the number "1" in the EVENING sequence section 44 because the dosage instructions for this prescription is "Take one tablet each day for high cholesterol." The "cyclobenzaprine" prescription label 40D of FIG. 6A includes dosage table 42 with "1" in each of the MORNING, NOON, and EVENING sequence sections 44 because the dosage instructions for this prescription is "Take one tablet three times daily as needed for mild pain." Finally, the "ibruprofen" prescription label 40E of FIG. 7A includes dosage table 42 with "1" in each of the sequence sections because the dosage instructions for this prescription is "Take four tablets each day for pain."

According to preferred embodiments, dosage tables 42 are pre-printed on the label stock supplied to the pharmacy and the dosage numbers 46 are printed in the dosage tables 42 at the same time the prescription information is printed on the remaining portion of the labels. In other words, the labels are supplied to pharmacies by a label supplier (which typically would be a provider of the present compliance system) with blank dosage tables 42 already printed on the supplied labels 40. Appropriate dosage numbers are then printed in the proper sequence sections 44 of each dosage table 42 by the pharmacy labeling software based on the dosage instructions entered into the pharmacy computer by the pharmacist at the time of dispensing the particular prescription. In preferred embodiments, the pharmacy software is modified to require the pharmacy to enter correct dosage numbers for each sequence section 44 via the pharmacy computer. In a less preferred embodiment and as shown in the present Figures, the pharmacist may handwrite the appropriate dosage numbers 46 into the appropriate sequence sections 44 of the pre-printed dosage tables 42. In yet another embodiment, the dosage table 42 and appropriate dosage numbers 46 are both printed by the pharmacy printer. This latter embodiment is less preferred as it both requires the pharmacy to have higher quality printers to print the dosage tables 42 with the sequence identifiers in color and is generally less efficient than supplying the labels to the pharmacy with blank dosage tables 42 already printed on the labels.

While dosage tables 42 may be provided on prescription labels 40 in any number of manners and positions, the dosage tables 42 are preferably connected to each label 40 using perforations 48 such that dosage table 42 may be printed and applied to a container with the with the standard prescription information or removed as desired by the user. This embodiment is particularly useful when labels 40 are supplied to a pharmacy on a label roll that fits into a dedicated printer as known in the art. In this regard, the separate but connected dosage table 42 allows the pharmacy to stock a single label type for both (1) prescriptions included as part of a Med-Sync program as described herein that includes dosage tables 42 on the containers (i.e., where a plurality of medications are prescribed to a patient and the patient intends to further dispense each of the medications into a corresponding pill tray 10); and (2) prescriptions in which the pharmacy does not wish to include the dosage table 50 such as single prescriptions, prescriptions for liquids or ointments, etc. It should be understood that this embodiment also allows a pharmacist to remove the dosage table 42 and apply it elsewhere on the container separately from the label 40. For example, for containers with smaller circumferences which would result in an overlap if label 40 is applied to the container as a whole, the perforations 48 permit the pharmacist to remove the dosage table 42 and apply it to the container where available space is provided. It should also be understood that label 40 could include multiple dosage tables 42 with one of the dosage tables 42 intended to be applied to the container with label 40 and another table 42 operable to be removed via perforations 48 for application on another substrate.

Figure 8:
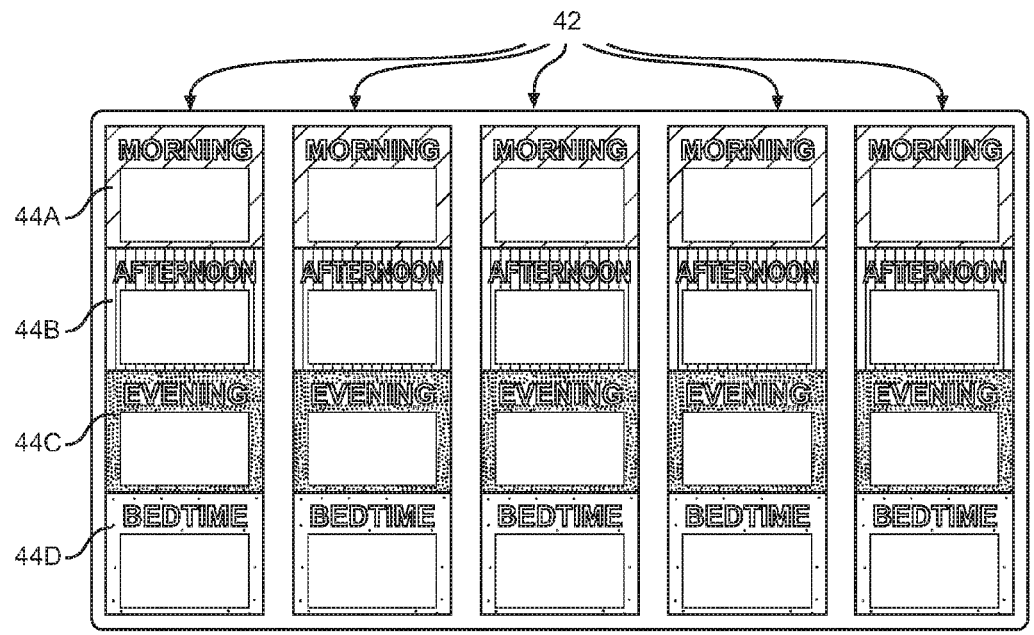
FIG. 8 depicts a sheet of dosage table stickers operable to be applied to a container according to one embodiment of the disclosure.
Figure 9:
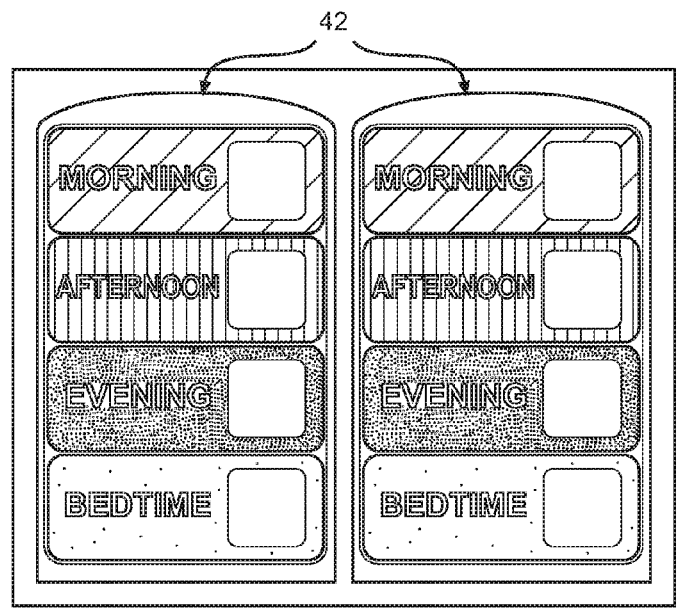
FIG. 9 depicts a sheet of larger dosage table stickers particularly suitable for application to one side of a triangular-shaped container according to one embodiment of the disclosure.

Referring to FIGS. 8-9, dosage tables 42 may also be provided to a pharmacy for application to a prescription container as a separate sticker distinct from the prescription label 40. For purposes of the present application, the term "sticker" as used herein refers to an adhesive substrate containing a dosage table 42, 52 that is not intended to be run through a printer for printing of subsequent information (i.e., all desired information printed by a printing machine is pre-printed by the supplier of the stickers). In contrast, a "label" as used herein refers to a substrate that is intended to be inserted into a printer of the dispensing entity for subsequent printing of at least some information at the pharmacy. It is noted that FIG. 8 depicts smaller dosage tables 42 for application to more traditional containers while FIG. 9 depicts a larger sized embodiment of dosage table 42 particularly suited to be applied to one side of a triangular shaped container such as disclosed in U.S. Patent Application Publication No. 2008/0262930, the entire contents of which is incorporated herein by reference. When used with triangular shaped containers, the container is preferably shipped with a sticker having dosage table 42 pre-applied to the container similar to how closures may be shipped to pharmacies with liners 50 having dosage tables 52 already installed on the closures as described below.

The sticker embodiment is particularly useful when a pharmacy's labeling software does not have the capability, or the pharmacy chooses not to modify its pharmacy labeling software to give it the capability, of printing appropriate dosage numbers 46 in the dosage tables 42 based on the dosage instructions of the prescription entered into the pharmacy computer. Thus, in this situation, the pharmacy could stock a plurality of stickers having pre-printed dosage tables 42 with blank sequence sections 44 (i.e., sequence sections with no dosage numbers 46) such that the dispensing entity can handwrite the appropriate dosage numbers 46 at the time of dispensing the prescribed medication. Alternately, the pharmacy could stock a plurality of stickers having pre-printed dosage numbers 46 in the sequence sections 44 of dosage table 42 corresponding to various potential prescription sequence schedules. Then, at the time of labeling and dispensing a particular prescription, a pharmacist can choose an appropriate dosage table 42 from the stock of stickers according to the dosage instructions of the particular prescription being dispensed. These two embodiments can also be combined where more common sequence schedules are provided on stickers with dosage tables 42 having pre-printed dosage numbers 46 while dosage tables 42 without pre-printed dosage numbers may be provided for uncommon sequence schedules to allow a pharmacist to handwrite the appropriate dosage numbers 46 when needed.

Referring to FIG. 3B, each dosage table 52 for the closures is preferably provided as a liner 50 able to inserted into upper and/or lower cavities of closures as described, for example, in U.S. Pat. No. 8,881,988, the entire contents of which is incorporated herein by reference. FIG. 3C is an example of a liner 50 for the glyburide prescription of label 40*a* inserted into an upper cavity of a non-reversible closure, while the '988 patent describes a similar embodiment having both a child resistant and non-child resistant configuration. Alternately, the closure may be configured as a two-piece cap as shown and described in, for example, U.S. Pat. Nos. 6,802,427 and 7,000,789, the entire contents of both being incorporated herein by reference. With respect to two-piece caps, an appropriate liner 50 may be inserted in the bottom of a clear inner cap such that it is visible through a donut hole in the top surface of the outer cap. It should be understood that other configurations of the closure could be provided that permit a liner 50 to be inserted into a cap cavity and visible to the patient without having to remove the closure from its container. In alternate embodiments, the liners 52 are printed on stickers that may be secured to the outer surface of a closure, particularly where the closure does not include a cavity to which an insert is visible when the closure is installed on a container. While not preferred, particularly due to the added time and expense in manufacturing the closures, it should be understood that the dosage table 52 may also be imprinted or embossed directly on the closures.

According to certain embodiments, whether the liners 50 are provided as inserts or stickers, a plurality of liners 50 may be provided to a pharmacy each having dosage numbers 56 pre-printed in dosage tables 52 according to potential dosage sequences as represented by FIGS. 3B, 4B, 5B, 6B, and 7B (which is not intended to depict a complete set). Alternately, closures are provided to the pharmacy that already include liners 50 with dosage tables 52 having pre-printed dosage numbers 56. When dispensing a prescription, the pharmacist then chooses an appropriate liner 50, or closure with the appropriate liner 50 already inserted in or adhesively applied to the closure, having a dosage table 52 to correspond with dosage table 42 of the particular prescription, or if dosage table 42 is not used, a dosage table 52 that corresponds with the standard dosing instructions of prescription label 40.

In other embodiments, the liners 50 having dosage tables 52 are delivered to the pharmacy without pre-printed dosage numbers 56. The pharmacy then prints or handwrites the appropriate dosage numbers 56 in the sequence sections 54 of the dosage table 52 at the time of dispensing the prescribed medication in the container system substantially as described above with respect to dosage tables 42. In particular, when closures are delivered to a pharmacy with liners 50, the liner 50 is operable to permit a pharmacist to handwrite the appropriate dosage numbers 56 in the sequence sections 54. However, when liners 50 are delivered in a form that requires application to a closure at the time of dispensing, the dosage numbers 56 may be printed by the pharmacy at the time the standard prescription label is printed (e.g., label 40 having dosage table 42 and liner 50 having dosage table 52 may be provided on a single label sheet that is run through a pharmacy printer such that the dosage numbers 46 and 56 are printed along with the remaining prescription information on label 40). Alternately, the pharmacy may handwrite the dosage numbers 56 in sequence sections 54 before or after the pharmacy applies the liner 50 to the closure. Whether the liners 50 are provided as liner inserts or stickers for the closures or imprinted/embossed directly on the closures, one important aspect of the liners 50 is that the color of the actual closure for each container system is preferably color neutral. In other words, each closure is preferably the same color (e.g., white) and is different than any of the colors of the sequence sections 54. Thus, a patient is unable to determine from the closure itself when the prescriptions housed in the particular container systems are to be taken. Instead, the patient will become trained to look at the dosage tables 42 and/or 52 of the container systems.

According to certain embodiments of the disclosure, dosage tables 42, 52 are disposed on the container systems as described above without utilizing pill tray 10. In this regard, dosage tables 42, 52 are useful for patients to quickly identify which medications need to be dispensed from particular container systems by identifying which sequence sections 44, 54 include actual dosage numbers 46, 56 during a particular sequence. For example, instead of taking medications from a sequence compartment 32 of a pill tray 10, a user will locate all prescription medications to be taken and how many pills of each during a particular sequence by looking for the appropriately colored sequence section 44, 54 of the dosage tables 42, 52 on the container systems to determine whether the sequence section 44, 54 includes a dosage number 46, 56 greater than "0."

According to another aspect of the disclosure, providing a dosage table 42 on both the container and a dosage table 52 on the closure allows the pharmacist or dispensing entity to quickly check to make sure an appropriate closure is installed on a container housing a particular prescribed medication by matching dosage table 52 of closure with dosage table 42 of the container. Similarly, if a patient removes the closures of two container systems at the same time, the patient will be able to look at the dosage table 42 of the container and match the appropriate closure to the container based on the dosage table 52 of the closure. This ability to match closures with the appropriate containers is critical as some users of the compliance system, particularly repeat users that are repeatedly prescribed the same medications, are likely to use dosage tables 52 of closures to dispense their prescribed medications with little reference or attention given to the prescription label 40 or dosage table 42 of the container.

Figure 10:
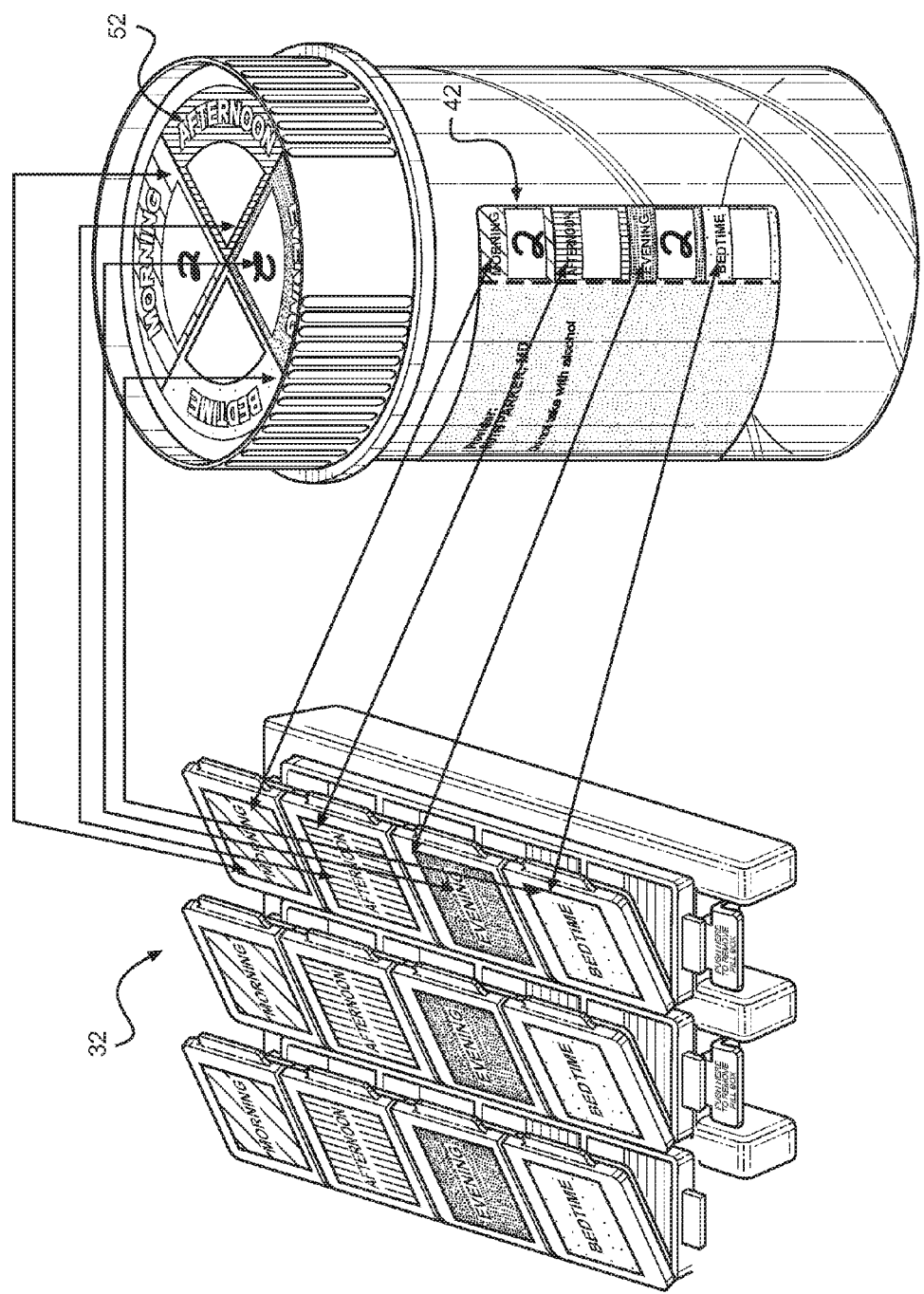
FIG. 10 depicts the container system of FIG. 3A juxtaposed with a portion of the pill tray of FIG. 2, exemplifying the sequence sections of the dosage tables being sequentially aligned with corresponding sequence compartments of the pill tray.

Referring to FIG. 10, dosage tables 42 and/or 52 on the container systems provide an intuitive approach to filling pill tray 10 by graphically representing the sequence compartments 32 of one daily section 30. Thus, the patient or caregiver is able to refer to the dosage tables 42, 52 of each container system to efficiently and effectively dose each of the sequence compartments 32 of the pill tray 10. In this regard, while each patient or caregiver may choose to use the system of the present disclosure according to their personal preferences, studies have shown that users will typically first use the appropriately colored sequence identifiers of the dosage tables 42, 52 to locate and provide the order in which the pill tray 10 is dosed. In particular, users typically start with the container systems having a dosage number 46, 56 in the MORNING sequence section 44, 54, and dose the mediations of these container systems according to the dosage numbers 46, 56 of the dosage tables 42, 52 until the appropriate number of pills of MORNING related containers have been dispensed into the appropriate sequence compartments 32 of the pill tray 10. The user will then move to container systems having dosage numbers 46, 56 in the AFTERNOON sequence section 44, 54 that have not been dispensed with the MORNING related containers (i.e., containers with an AFTERNOON dosage number that does not also include a MORNING dosage number), and so forth until all the medications of the patient's Med-Sync program have been dispensed into the appropriate sequence compartments 32 of the pill tray 10.

For example, with respect to the prescriptions of FIGS. 3A-7A, a patient will typically locate a container system containing a dosage number 46, 56 in the blue MORNING sequence section 44, 54 such as the glyburide prescription. Referring to FIG. 10, the user then takes the glyburide prescription container as shown in FIG. 3C and dispenses the glyburide pills into each of the daily sections 30 of the pill tray 10 according to dosage table 42, 52—2 pills in each sequence compartment 32a having the blue MORNING indicia 35 and 2 pills in each sequence compartment 32c having black EVENING indicia. The user then sets aside the glyburide prescription container, locates another container system containing a dosage number 46, 56 in the blue MORNING sequence section 44, 54 such as the lisinopril prescription container as shown in FIG. 4C, and dispenses the lisinopril pills into the appropriate sequence compartments according to dosage table 42, 52—1 pill in each sequence compartment 32a having blue MORNING indicia 35. The user next sets aside the lisinopril prescription container, locates another container system containing a dosage number 46, 56 in the blue MORNING sequence section 44, 54 such as the cyclobenzaprine prescription container of FIG. 6C, and dispenses the cyclobenzaprine pills into the appropriate sequence compartments according to dosage table 42, 52—1 pill in each sequence compartment 32a having blue MORNING indicia, 1 pill in each sequence compartment 32b having red AFTERNOON indicia, and 1 pill in each sequence compartment 32c having black EVENING indicia. The user then sets aside the cyclobenzaprine prescription container system, locates the last container system containing a dosage number 46, 56 in the blue morning sequence section 44, 54, the ibuprofen prescription container of FIG. 7C, and dispenses the ibuprofen pills into appropriate sequence compartments according to dosage table 42, 52—1 pill in each sequence compartments 32a-32d. The user then sets aside the ibuprofen container system and looks for any other container systems having a dosage number 46, 56 in the blue MORNING sequence section 44, 54. As there are no more container systems containing pills to be taken in the morning, the user looks for any container systems with a dosage number 46, 56 in the red AFTERNOON sequence section 44, 54. According to this example, there are none because the only medications to be taken in the afternoon is cyclobenzaprine and ibuprofen, but they were already dispensed into sequence compartments 32b as they were also prescribed for the morning. Thus, the user next locates container systems with a dosage number 46, 56 in the black EVENING sequence sections 44, 54, the atorvastatin container of FIG. 5C, and dispenses the atorvastatin pills in sequence compartments 32c having black EVENING indicia. According to this example, the user then knows he has dispensed all the prescribed medications into appropriate sequence compartments 32 of the pill tray 10 because there are no other container systems having dosage numbers 46, 56 in the black EVENING or green BEDTIME sequence sections 44, 54 that have not already been dispensed in the pill tray and set aside.

As will be recognized, a particular advantage of the present compliance system described above is that it is inexpensive for a dispensing entity to implement as it does not require any new equipment (such as expensive "blister" or "pouches" packaging equipment that separates pills into individually sealed compartments corresponding to days in which the medication is to be taken). Nor is it time consuming for the dispensing entity, particularly when the pharmacy software is modified to automatically print the dosage numbers 46 directly on each prescription label 40. Further, it is simple for a patient to use as the simplified dosage instructions are consistent for each prescribed medication and are contained on the very same container system in which the medications would already be dispensed.

The foregoing description of preferred embodiments for this disclosure have been presented for purposes of illustration and description. They are not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A prescription compliance system for improving patient compliance in taking a plurality of prescribed medications, each of the plurality of prescribed medications to be housed in one of a plurality of prescription container systems and each having dosing instructions providing that the prescribed medication is to be taken according to a sequence schedule, the prescription compliance system comprising:

a pill tray including at least one frequency section and a plurality of sequence compartments within each frequency section, the plurality of sequence compartments configured for receiving the plurality of prescribed medications according to the sequence schedule of each of the plurality of prescribed medications; and a prescription container labeling system including a plurality of dosage tables each configured to be applied to one of the prescription container systems, each dosage table including a plurality of demarcated sequence sections sequentially aligned with the plurality of sequence compartments of the at least one frequency section of the pill tray and each of the demarcated sequence sections configured to receive a dosage number identifying how many pills of the prescribed medication in the container system to which the dosage table is applied should be dosed to the corresponding sequence compartment of the at least one frequency section of the pill tray to provide graphical dosage instruction information for the patient in dosing each of the sequence compartments of the pill tray with each of the plurality of prescribed medications.

2. The prescription compliance system of claim 1 wherein the prescription container labeling system includes a plurality of blank prescription labels for subsequent printing of prescription specific information at a dispensing entity, each of the blank prescription labels including one of the plurality of dosage tables printed thereon without dosage numbers in the plurality of demarcated sequence sections such that the dosage tables are configured to receive the dosage numbers at the dispensing entity.

3. The prescription compliance system of claim 1 wherein the prescription container labeling system includes a roll of blank prescription labels for subsequent printing of prescription specific information at a dispensing entity, each blank prescription label including a first distinct section for printing of traditional prescription information and a second distinct section including one of the plurality of dosage tables.

4. The prescription compliance system of claim 3 wherein the first distinct section of each blank prescription label is separated from the second distinct section by a perforated line such that the first and second distinct sections are operable to be applied together to one of the prescription container systems or the second distinct section may be removed from the first distinct section.

5. The prescription compliance system of claim 1 wherein the prescription container labeling system includes a plurality of stickers for distribution to a dispensing entity, each of the plurality of stickers including one of the plurality of dosage tables printed thereon and dosage numbers printed in the plurality of demarcated sequence sections of each dosage table according to potential sequence schedules for the plurality of prescribed medications.

6. The prescription compliance system of claim 1 wherein the prescription container labeling system includes a plurality of stickers for distribution to a dispensing entity, each of the plurality of stickers including one of the plurality of dosage tables printed thereon without dosage numbers printed in the plurality of demarcated sequence sections such that the dosage tables of the stickers are configured to receive handwritten dosage numbers at the dispensing entity.

7. The prescription compliance system of claim 1 wherein the dosage tables are applied to a closure of the prescription container system.

8. The prescription compliance system of claim 7 wherein the dosage tables are disposed on a liner inserted into a cavity of the closure.

9. The prescription compliance system of claim 7 wherein the dosage tables are distributed to a dispensing entity without dosage numbers printed in the plurality of demarcated sequence sections such that the dosage tables are configured to receive handwritten dosage numbers at the dispensing entity.

10. The prescription compliance system of claim 7 wherein the prescription container labeling system further comprises a second dosage table applied to a container of the container system, the dosage numbers of the second dosage table matching the dosage numbers of the dosage table applied to the closure.

11. The prescription compliance system of claim 1 wherein each of the sequence compartments of one of the frequency sections of the pill tray are assigned sequence identifiers in assigned colors and each of the demarcated sequence sections of the dosage tables include colored sequence identifiers matching the sequence identifiers of the corresponding sequence compartments of the pill tray.

12. A method for improving patient compliance in taking a plurality of prescribed medications each having prescription instructions providing that the prescribed medication is to be taken each day according to a sequence schedule, the method comprising:
providing a pill tray to a patient including at least one frequency section and a plurality of sequence compartments within each frequency section, the plurality of sequence compartments configured for receiving the plurality of prescribed medications according to the sequence schedule of each of the plurality of prescribed medications; and
dispensing each of the plurality of prescribed medications to the patient in a prescription container system, the dispensing step including, for each prescribed medication, applying a dosage table to the prescription container system in which the prescribed medication is dispensed, the dosage table including a plurality of demarcated sequence sections sequentially aligned with the plurality of sequence compartments of the at least one frequency section of the pill tray and each of the demarcated sequence sections including a dosage number identifying how many pills of the prescribed medication should be dosed to the corresponding sequence compartments of the pill tray,
wherein the dosage tables for each prescribed medication provide graphical dosage instruction information for the patient in dosing each of the sequence compartments of the pill tray according to the sequence schedules of each of the plurality of prescribed medications.

13. The method of claim 12 further comprising receiving from a label supplier a plurality of blank prescription labels for subsequent printing of prescription specific information at a dispensing entity, each of the blank prescription labels including the dosage table printed thereon without dosage numbers in the plurality of demarcated sequence sections such that the dispensing step further includes providing the dosage numbers to the dosage table.

14. The method of claim 13 wherein the dosage numbers are printed in the plurality of demarcated sequence sections with the prescription specific information based on prescription information entered into a pharmacy computer.

15. The method of claim 12 further comprising receiving from a label supplier a roll of blank prescription labels for subsequent printing of prescription specific information at a dispensing entity, each blank prescription label including a first distinct section for printing of traditional prescription information and a second distinct section including the dosage table to be applied to one of the prescription container systems.

16. The method of claim 15 wherein the first distinct section of each blank prescription label is separated from the second distinct section by a perforated line such that the first and second distinct sections are operable to be applied together to one of the prescription container systems or the second distinct section may be removed from the first distinct section.

17. The method of claim 12 further comprising receiving from a label supplier a plurality of stickers, each of the plurality of stickers including one of the dosage tables printed thereon and dosage numbers printed in the plurality of demarcated sequence sections of each dosage table according to potential sequence schedules for the plurality of prescribed medications, the dispensing step including choosing one sticker from the plurality of stickers for application to the prescription container system according to the dosage schedule of the prescribed medication being dispensed and the dosage numbers of the stickers.

18. The method of claim 12 further comprising receiving from a label supplier a plurality of stickers, each of the plurality of stickers including one of the plurality of dosage tables printed thereon without dosage numbers printed in the plurality of demarcated sequence sections, the dispensing step further including handwriting of the dosage numbers in the dosage tables.

19. The method of claim 12 wherein, for each prescribed medication, the dosage table is applied to a container of the container system and the dispensing step further includes applying a closure to the container, the closure including a second dosage table matching the dosage table applied to the container to which the closure is applied.

20. The method of claim 19 wherein the dispensing step further includes, for each prescribed medication, handwriting dosage numbers on the dosage table of the closure that match the dosage numbers of dosage table applied to the container to which the closure is applied.

21. The method of claim 12 wherein each of the sequence compartments of one of the frequency sections of the pill tray are assigned sequence identifiers in assigned colors and each of the demarcated sequence sections of the dosage tables include colored sequence identifiers matching the sequence identifiers of the corresponding sequence compartments of the pill tray.

* * * * *